(12) United States Patent
Van Gogh et al.

(10) Patent No.: US 8,374,685 B2
(45) Date of Patent: *Feb. 12, 2013

(54) SYSTEM, COMPUTER-READABLE MEDIUM, METHOD, AND USE FOR COMBINED EPITHELIAL EARLY CANCER DIAGNOSIS AND STAGING

(75) Inventors: Antonius Theodorus Martinus Van Gogh, 's-Hertogenbosch (NL); Bernardus Hendrikus Wilhelmus Hendriks, Eindhoven (NL); Hans Zou, Windsor, NJ (US); Maarten Marinus Johannes Wilhelmus Van Herpen, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 684 days.

This patent is subject to a terminal disclaimer.

(21) Appl. No.: 12/529,552

(22) PCT Filed: Mar. 7, 2008

(86) PCT No.: PCT/IB2008/050835
§ 371 (c)(1), (2), (4) Date: Sep. 10, 2009

(87) PCT Pub. No.: WO2008/110968
PCT Pub. Date: Sep. 18, 2008

(65) Prior Publication Data
US 2010/0056927 A1 Mar. 4, 2010

Related U.S. Application Data

(60) Provisional application No. 60/894,270, filed on Mar. 12, 2007.

(51) Int. Cl.
*A61B 6/08* (2006.01)
*G01J 4/00* (2006.01)
*G01J 3/447* (2006.01)
*G01N 21/47* (2006.01)

(52) U.S. Cl. .......... 600/478; 600/476; 600/477; 356/73; 356/364; 356/369; 250/559.09; 250/225

(58) Field of Classification Search ........................ None
See application file for complete search history.

(56) References Cited

U.S. PATENT DOCUMENTS
6,091,983 A 7/2000 Alfano et al.
(Continued)

FOREIGN PATENT DOCUMENTS
WO 2005029051 A1 3/2005

OTHER PUBLICATIONS

Amelink et al. "Differential pathlength spectroscopy: A novel technique to determine the local optical properties of tissue in vivo", Conference Paper, Biomedical Topical Meeting (BIO), Miami Beach, Florida, Apr. 14, 2004.*

(Continued)

*Primary Examiner* — Long V. Le
*Assistant Examiner* — Farshad Negarestan

(57) ABSTRACT

A system (40) for diagnosis and staging of early stages of cancer in the tissue of a patient is provided. The system—is configured to combine information from a Polarized Light Scattering Spectroscopy measurement (70) having a first probe depth, and a Differential Path Length Spectroscopy measurement (60) having a second probe depth, wherein the second probe depth is set larger than' the first probe depth. By comparing the results of the Polarized Light Scattering Spectroscopy and Differential Path Length Spectroscopy measurements early stages of cancer, such as dysplasia may be detected. Also hyperplasia, carcinoma in situ, and carcinoma may be detected. A computer-readable medium, method and use are also provided.

18 Claims, 6 Drawing Sheets

U.S. PATENT DOCUMENTS

| | | |
|---|---|---|
| 2002/0143243 A1 | 10/2002 | Georgakoudi et al. |
| 2002/0171831 A1 | 11/2002 | Backman et al. |
| 2003/0232445 A1 | 12/2003 | Fulghum |
| 2006/0063985 A1 | 3/2006 | Hogan |
| 2006/0155178 A1 | 7/2006 | Backman et al. |
| 2006/0247532 A1 | 11/2006 | Ramanujam et al. |

OTHER PUBLICATIONS

So et al: "Two-Photon Deep Tissue Ex Vivo Imaging of Mouse Dermal and Subcutaneous Structures"; Optics Express, vol. 3, No. 9, Oct. 26, 1998, pp. 339-350.

Workshop on Biophotonics and Molecular Simulations (WBMS): Program and Abstract Book; 2006, 1st Joint Workshop on Biophotonics and Molecular Simulations, Sep. 9-12, 2006, Organized by the International Laser Centre, European Society for Photobiology and Slovak Biophysical Society, 97 Page Document.

Backman et al: "Polarized Light Scattering Spectroscopy for Quantitative Measurement of Epithelial Cellular Structures In Situ"; IEEE Journal of Selected Topics in Quantum Electronics, vol. 5, No. 4, Jul./Aug. 1999, pp. 1019-1026.

\* cited by examiner

SYSTEM, COMPUTER-READABLE MEDIUM, METHOD, AND USE FOR COMBINED EPITHELIAL EARLY CANCER DIAGNOSIS AND STAGING

CROSS REFERENCE TO RELATED CASES

Applicants claim the benefit of International Application Number PCT/IB2008/050835, filed Mar. 7, 2008, and United States Provisional Application Ser. No. 60/894,270, filed Mar. 12, 2007.

FIELD OF THE INVENTION

This invention pertains in general to the field of medical diagnostics. More particularly the invention relates a system, computer-readable medium, and method for early cancer detection and staging by combined Differential Path Length Spectroscopy and Polarized Light Scattering Spectroscopy.

BACKGROUND OF THE INVENTION

Cancer is one of the top three causes of death in the world. Of all cancers, more than 85% have epithelial origin, meaning that they pertain close to the surface. An example is the skin. Skin is composed of three primary layers: the epidermis, which provides waterproofing and serves as a barrier to infection; the dermis, which serves as a location for the appendages of skin; and the hypodermis, a subcutaneous adipose layer, which is also called the basement membrane.

Epidermis is the outermost layer of the skin. It forms the waterproof, protective wrap over the body's surface and is made up of stratified squamous epithelium with an underlying basal lamina.

In between epidermis and dermis the basal layer or Stratus basale is located consisting of a single layer of tall, simple columnar epithelial cells lying on a basement membrane. These cells undergo rapid cell division, mitosis to replenish the regular loss of skin by shedding from the surface. About 25% of the cells are melanocytes, which produce melanin that provides pigmentation for skin and hair.

The dermis is the layer of skin beneath the epidermis that consists of connective tissue and cushions the body from stress and strain. The dermis is tightly connected to the epidermis by the basal layer. The blood vessels in the dermis provide nourishment and waste removal to its own cells as well as the basal layer of the epidermis.

The hypodermis is not part of the skin, and lies below the dermis. Its purpose is to attach the skin to underlying bone and muscle as well as supplying it with blood vessels and nerves.

Apart from the skin several other epithelial cancer types exists, among others lung cancer, cervical cancer, gastrointestinal cancer, and skin cancer. The epithelial cancer development may be characterized in different stages.

In the hyperplastic stage, the morphology of cells does not change, only the number of epithelial layers, and hence the thickness of epidermis changes.

In the dysplastic stage, cells change in shape and size. Furthermore, there is clear evidence for an increase in the pre-malignant epithelial microvascular blood content in dysplasia, so-called angiogenesis, which is not typical in benign tumors in hyperplastic stage. Therefore, angiogenesis is a unique mark for malignant hyperplasia. Additionally, blood oxygen content has decreased in late dysplasia or carcinoma.

In the carcinoma in situ stage, cell morphology has changed even further and aberrant cells have spread throughout the epidermis. Finally, in the carcinoma stage, cancer cells have crossed the basal layer and may spread, or metastasize, throughout the body.

Differential Path Length Spectroscopy (DPS) (see patent application WO 2005/029051) is an optical technology for cancer detection, in cancers such as breast cancer, oral cancer, and brain cancer. It is a fiber-optic technique in which white light is delivered to the tissue by a delivery-collection (DC) fiber. Part of the light is backscattered by the turbid tissue and is measured by two fibers, i.e., the DC fiber and a collection fiber, which is glued to the DC fiber. The actual signal is the difference between the signals of the two fibers. Subtraction of the two signals reduces the presence in the signal of multiple-scattered photons, and in this way the probe depth is reduced. DPS measures tissue properties from single and multiple-scattered photons, with a constant probe depth that may be tuned by choosing a particular fiber diameter. The constant path length enables absolute measurement of blood oxygenation, blood amount, average blood vessel diameter and scattering, all of which are changed when tissue becomes cancerous. A disadvantage of DPS is that it is not well suited for early detection of tissue aberrations, because three out of four parameters only change significantly when cancer has already developed. For example, in the hyperplastic stage, blood oxygenation, amount of blood, and the average vessel diameter will not have changed yet. Only the scattering is influenced in the hyperplastic stage. However, the DPS modality is not very sensitive to a change in this parameter.

Another known technology for cancer detection is Polarized Light Scattering Spectroscopy (LSS) (see V. Backman et al., IEEE J. Selected Topics Quantum Electron., Vol. 5, No 4, July/August 1999, p. 1019). The principle of LSS is that linearly polarized light from a white light source is incident on the tissue to be investigated. Diffusely scattered light is detected and the intensity of both polarization components is measured. The principle of the technique is based on the fact that photons that scatter once or twice will mostly retain their polarization, whereas multiple scattered photons will lose their polarization. Hence, by subtracting the two measured light intensities $I_\perp$ and $I_\|$ the contribution of the multiple scattered photons will cancel. LSS spectra of tissue may be modeled with Mie theory and by fitting of experimental spectra it is possible to obtain three parameters: the average cell size, standard deviation in cell size, and the refractive index of the tissue. It has been shown that these three parameters are different for malignant tissue and may be used for cancer detection. A disadvantage of LSS is that it is not sensitive to detection of early stages of cancerous tissue as the maximum imaging depth or probe depth is limited such that it is only possible to image a limited part of the epidermis. This makes LSS insensitive to the hyperplastic stage as the layer thickening of the epidermis in the hyperplastic stage may not be measured. Furthermore, due to the limited probe depth of LSS no scattering information is obtained from below the epithelial layer, which is important in differentiating between carcinoma in situ and carcinoma.

Accordingly, both the DPS modality and LSS modality have disadvantages regarding the suitability in detecting early stages of cancer development. Hence, an improved system, computer-readable medium, method, and use for early cancer diagnosis or staging would be advantageous.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a system, computer-readable medium, method, and use according to the appended patent claims.

According to one aspect of the invention, a system for detection of early stages of epithelial cancer in a tissue of a patient is provided. The system comprises a Polarized Light Scattering Spectroscopy unit for performing a Polarized Light Scattering Spectroscopy measurement having a first probe depth, resulting in a first spectrum. Moreover, the system comprises a Differential Path Length Spectroscopy unit for performing a Differential Path Length Spectroscopy measurement having a second probe depth, resulting in a second spectrum, wherein the second probe depth is larger than the first probe depth. Furthermore, the system comprises a processing unit for calculation of a first correlation parameter value based on a correlation calculation of the first spectrum with a first reference spectrum, and a second correlation parameter value based on a correlation calculation of the second spectrum with a second reference spectrum, wherein the first correlation value in relation to the second correlation value is indicative of the cancer stage of the tissue.

According to another aspect of the invention, a computer-readable medium having embodied thereon a computer program for processing by a processor. The computer program comprises a first code segment for performing a Polarized Light Scattering Spectroscopy measurement having a first probe depth, resulting in a first spectrum. Moreover, the computer program comprises a second code segment for performing a Differential Path Length Spectroscopy measurement having a second probe depth, resulting in a second spectrum, wherein the second probe depth is larger than the first probe depth. Furthermore, the computer program comprises a third code segment for calculating a first correlation parameter value based on a correlation calculation of the first spectrum with a first reference spectrum, and a second correlation parameter value based on a correlation calculation of the second spectrum with a second reference spectrum, wherein the first correlation value in relation to the second correlation value is indicative of the cancer stage of the tissue.

According to yet another aspect of the invention a method for detection of early stages of epithelial cancer in a tissue of a patient is provided. The method comprises performing a Polarized Light Scattering Spectroscopy measurement having a first probe depth, resulting in a first spectrum. Moreover, the method comprises performing a Differential Path Length Spectroscopy measurement having a second probe depth, resulting in a second spectrum, wherein the second probe depth is larger than the first probe depth. Furthermore, the method comprises calculating a first correlation parameter value based on a correlation calculation of the first spectrum with a first reference spectrum, and a second correlation parameter value based on a correlation calculation of the second spectrum with a second reference spectrum, wherein the first correlation value in relation to the second correlation value is indicative of the cancer stage of the tissue.

According to still another aspect of the invention a use of the system, computer-readable medium, or method according to any one of the appended claims 1-18, for diagnosis and staging of epithelial early cancer aberrations is provided.

The present invention may according to some embodiments be applied for detection of epithelial cancers, tissue aberrations that may lead to cancer, or tissue aberrations that may indicate, or lead to other disorders. The fiber diameter, and indirectly the DPS probe depth, should be chosen according to the epidermis thickness of the particular tissue under study.

An object of the invention is to provide a system, method, computer-readable medium, combining information from a LSS measurement having a first probe depth, and a DSP measurement having a second probe depth, wherein the second probe depth is set larger than the first probe depth. By comparing the results of the LSS and DPS measurements early stages of cancer, such as dysplasia may be detected. Also hyperplasia, carcinoma in situ, and carcinoma may be detected utilizing the present invention.

The present invention may according to some embodiments be used to detect early stages of cancer, such as epithelial cancer. In some embodiments the present invention may be used to detect early stages of skin cancer. However, the present invention is not limited to only skin cancer, but may be just as well utilizes to detect early stages of esophagus cancer, mouth cancer, cancer in the intestines, bladder cancer, cervix cancer, or any other cancer etc.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

Figure 1:
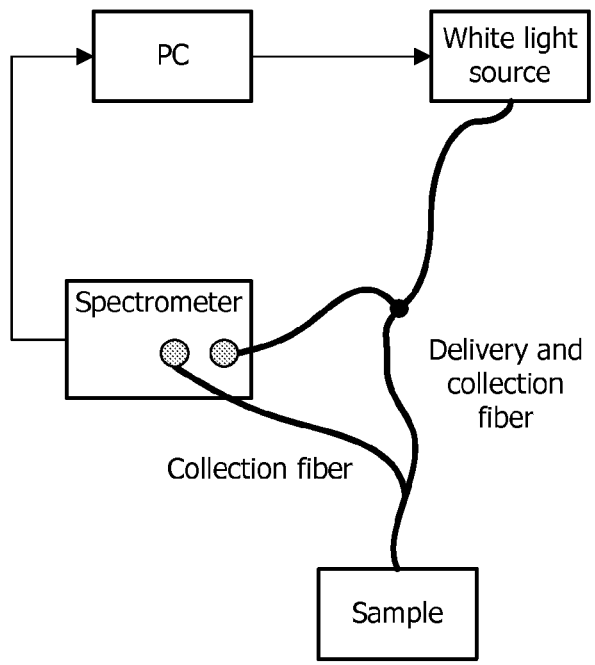
FIG. 1 is a schematic overview of a commonly known DPS set-up.

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention. FIG. 1 illustrates the principle for a commonly known Diffuse Path Length Spectroscopy set-up. The DPS modality may be utilized in two modes, the single scattering regime or the multiple scattering regime. It has been shown that the photon path length l for the single scattering regime follows $l=2\, l_{mfp}=2/\mu_s$, meaning that the photon path length is inversely proportional to the scattering coefficient $\mu_s$ of the medium being analyzed. Moreover, based on utilizing absorption constant $\mu_a(\lambda)$ for tissue in the range of $0<\mu_a<2$ mm$^{-1}$ and the scattering constant $\mu_s(\lambda)$ for tissue in the range of $10<\mu_s<100$ mm$^{-1}$, the constant path length l has been shown to follow $l=0.80*d_{fiber}$. This means that the photon path length in the multiple scattering regime is dependent of the fiber core diameter of the delivery-collection (DC) fiber. Accordingly, by changing the diameter of the fiber core it is possible to image tissue at various depths from the tissue surface. In other words, the probe depth $z_{max}=l/2$, may be tuned by choosing a particular fiber core diameter.

Measurements have shown that 98% of a measured Polarized Light Scattering Spectroscopy signal comes from a probe depth z given by $\tau=\mu_s z<2$, where $\tau$ is the optical thickness. Hence, a photon propagating through a medium with $\tau=1$ will undergo one scattering event on average. In other words, the probe depth $z_{max}$ is equal to $2/\mu_s$. Based on the criteria that the linearly polarized white light incident on the tissue is within the wavelength range of 350 and 800 nm, and the scattering constant $\mu_s$ of the epidermis is within the range of $42<\mu_s<110$ mm$^{-1}$, and the scattering constant $\mu_s$ for dermis is within the range of $18<\mu_s<46$ mm$^{-1}$, the probe depth $z_{max}$ may be obtained via experiments to be within the range of $18<z_{max}<48$ µm. Hence LSS may only probe the epidermis. Contrary to DPS, the probe depth is not constant and depends on the scattering properties of the turbid medium.

The following description focuses on embodiments of the present invention applicable to early cancer detection and staging and in particular to an early cancer detection and staging by using a combination of DPS and LSS.

The present invention provides a combination technology of LSS and DSP for the detection of early tissue aberrations, which may be used for cancer staging. Moreover, the present invention may according to some embodiments improve detection of tissue aberrations even in the hyperplastic stage to improve cancer staging. A concept of some embodiments of the present invention is to set the probe depth of the DPS measurement larger than the probe depth of the LSS measurement. In this way it will be possible to utilize information from both the LSS measurement and the DPS measurement to improve the staging of early cancer diagnosis. This technical effect is not possible by merely performing two separate measurements of DPS and LSS, respectively, as the result of utilizing each modality one results in one information, respectively, which may not be used for significant detection of early stages of cancer.

As mentioned above the probe depth for the LSS modality is smaller than the thickness of the epidermis and as a consequence no information may be retrieved from LSS concerning the thickness of the epidermis that is an indication that the investigated tissue is in the hyperplastic stage and is in the first stage of cancer development. It is important to notice that the investigated tissue may be in the hyperplastic stage even without being in the first stage of cancer development. For example, if there is a wound on the surface of the skin, the it is natural for the tissue to enter the hyperplastic stage for creating new cells which will eventually replace the damage cells on the surface of the skin.

Figure 2:
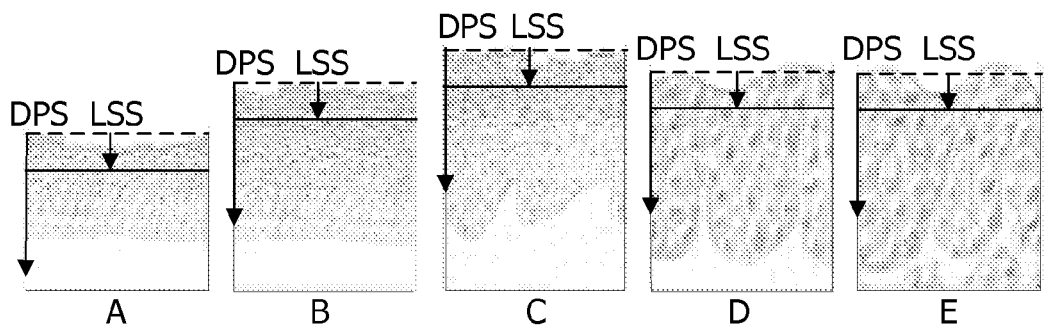
FIG. 2 is an illustration showing an embodiment.

FIG. 2 illustrates the concept of some embodiments of the invention wherein the DPS probe depth is set larger than the LSS probe depth by varying the fiber diameter core. FIG. 2 is a schematic illustration of the different stages of the skin, normal mucosa (A), hyperplastic stage (B), dysplastic stage (C), carcinoma in situ (D), and carcinoma (E). As may be observed from FIG. 2 the probe depth of the DPS measurement is set larger than the LSS measurement. In this way it is possible to discriminate between the early stages of cancer. When utilizing the invention according to some embodiments, the normal mucosa may be used as reference or calibration to facilitate the discrimination of the later stages of cancer. In the hyperplastic stage the LSS measurement signal will still be substantially equal as compared to the normal mucosa due to the fact that the cell size and shape still have not changed considerably. However, the DPS measurement, configured with a probe depth being set e.g. beneath the basal layer when the tissue is normal, will now probe close to the basal layer because of the thickening of the epithelial layer. As a result the thickness of the epithelial layer may be deduced. Together with the results from the LSS measurement the investigated tissue may be characterized as being in the hyperplastic stage. In the dysplastic stage the LSS measurement signal start to change compared to the measurement signal for the normal mucosa and hyperplastic stage. For the LSS measurement this is mainly due the start of increase in cell size and shape that leads to more scattering. Also, the DPS measurement signal changes, as there is an increase of vascular structures and oxygenation of blood in the connective tissue beneath (but close to) the basal layer. Utilizing both results enables for detection of the dysplastic stage. In this way it is possible to discriminate between the hyperplastic stage and the dysplastic stage. In carcinoma in situ, cell morphology has changed even further and aberrant cells have spread throughout the epidermis and this will result in a different measurement signal for both LSS in terms of increased cell size and shape, and DPS in terms of more blood vessels. By utilizing both signals it is possible to discriminate the carcinoma in situ stage from the other stages of cancer. In the carcinoma stage, cancer cells have crossed the basal layer and may spread, or metastasize, throughout the body. This may be detected with the DPS measurement by even further blood vessels below the basal layer region.

As may be observed from FIG. 2, differentiating between carcinoma in situ and carcinoma is difficult with LSS, due to its limited probe depth. With LSS information of superficial tissue layers is obtained, whereas DPS measures information from deeper layers.

Utilizing the invention according to some embodiments will provide a way to discriminate between carcinoma in situ and carcinoma from hyperplasia and dysplasia.

In an embodiment a system is provided utilizing combined LSS measurement and DPS measurement. The fiber diameter is chosen such that the DPS probe depth is in the dermis and hence the signal consists of contributions from both epidermis and dermis. With $z_{max}=0.40*d_{fiber}$ and an epidermis thickness of 100 um, a fiber diameter larger than 400 um is required. As an example, a DPS fiber diameter of 800 um may be chosen such that the DPS probes 200 um deep into the tissue. In the case of normal, healthy tissue both the resulting LSS and DPS spectrum will resemble healthy tissue. In case of hyperplasia, i.e. the tissue being in the hyperplastic stage meaning increased cell division stage, the LSS spectrum will still resemble healthy tissue. However, the DPS spectrum will be different, because the thickened epidermis will result in that a larger part of the signal originates from the epidermis.

If the investigated tissue is cancerous in the dysplastic stage, the LSS measurement will detect the first changes in size and shape of cells. The detection limit of these changes may be lowered by correlating changes in the LSS spectrum with changes in the DPS spectrum. This may e.g. be performed by a processing unit 43, explained more in detail below, utilizing a correlation integral, or principal component analysis of spectra measured on a set of certified test samples, i.e. reference samples. This means that the LSS spectrum and DPS spectrum may separately be compared with the reference LSS spectrum and the reference DPS spectrum, respectively, of the reference samples in order to establish the cancer stage of the investigated tissue. After the LSS spectrum and DPS spectrum have been correlated with their corresponding reference spectrums, the results, hereinafter also denoted correlation value(s), are indicative of the stage of cancer in the investigated tissue. As an example, the result of correlating the measured LSS spectrum with its LSS reference spectrum may point to that the tissue is in the normal stage. However, the correlation between the measured DPS spectrum and its DPS reference spectrum may be indicative to the hyperplastic stage. These two results are the compared to indicate the stage of the skin, which in this example will be the hyperplastic stage, as the top layer of the skin still looks normal while the thickening of the basal layer, has started. Furthermore, the amount of roughening of the basal layer, which is not detected with LSS and thus invisible in the LSS spectrum, may be detected from the DPS spectrum, e.g. by monitoring signal variation levels when measured at various positions. In another example, the LSS correlation may be indicative that the tissue is in the dysplastic phase as the cells have started to change in size and shape while the DPS correlation is indicative that the tissue may also be in the dysplatic phase. Hence in this example the tissue may be diagnosed as dysplastic. In this case, even if the DPS correlation would be indicative to the hyperplastic stage, perhaps as a result of no detectable increased vascularity in the specific region of the DPS measurement while the thickening of the basal layer is detected, the tissue may be diagnosed as being in the dysplastic stage as the LSS correlation has detected increased cell size and changed cell shape. Using the same approach is it possible to discriminate between all of the aforementioned cancer stages by utilizing the invention according to some embodiments.

In an embodiment, when the investigated tissue will be in the carcinoma in situ stage, the LSS measurement will result in further changes in size and shape of cells. The DPS measurement signal will give additional information on the thickness of the cancerous epidermis and the roughness of the basal layer.

The difference between advanced stage carcinoma in situ and early stage carcinoma is that in the latter stage, cancerous cells have crossed the basal layer into the dermis. An LSS measurement alone is not able to detect this course of events. However, the DPS signal will reflect the changes in optical properties of the dermis.

Figure 3:
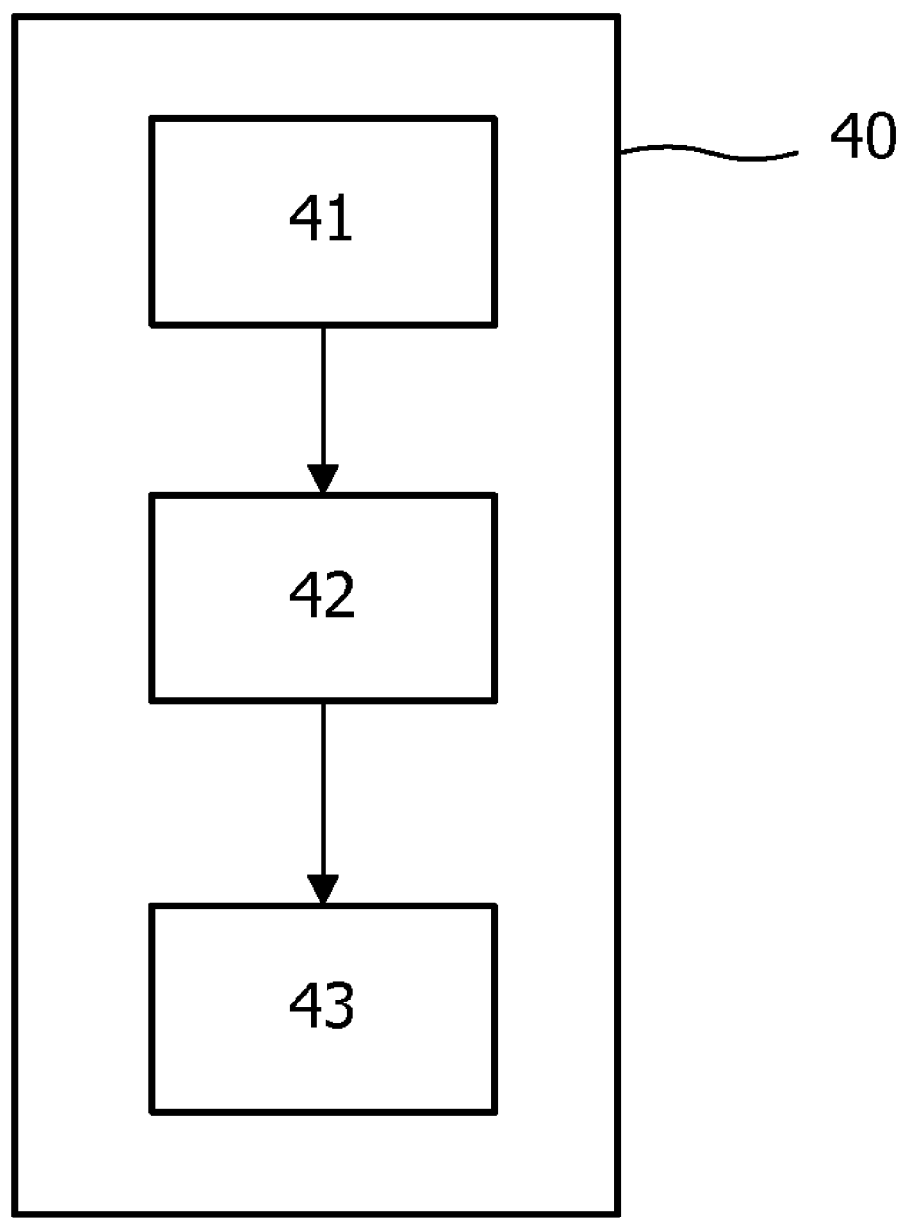
FIG. 3 is a block diagram showing a system according to an embodiment.

In an embodiment according to FIG. 3 a system (40) for detection of early stages of epithelial cancer in a tissue of a patient is provided. The system comprises a LSS unit 41 for performing a separate LSS measurement having a first probe depth. The LSS measurement results in a first spectrum. Moreover the system comprises a DPS unit 42 for performing a separate DPS measurement, having a second probe depth being set larger than the first probe depth by varying the fiber core diameter of the DC fiber, optionally at the same position as for the LSS measurement. The DPS measurement results in a second spectrum. Furthermore, the system comprises a processing unit 43 for calculation of a first correlation parameter value based on a correlation calculation of the first spectrum with a first reference spectrum, and a second correlation parameter value based on a correlation calculation of the second spectrum with a second reference spectrum. The first correlation value in relation to the second correlation value is then indicative of the cancer stage of the investigated tissue. The first and second reference spectra may comprise derived quantities with a database containing spectra and quantities of a set of samples, i.e. parameter reference value(s), that have been certified by a histopathologist. In some embodiments this processing may be performed visually by an expert, however in other embodiments the processing may be performed automatically by means of computer software, as it may be hard to detect the hyperplastic stage or dysplastic stage visually.

Figure 4:
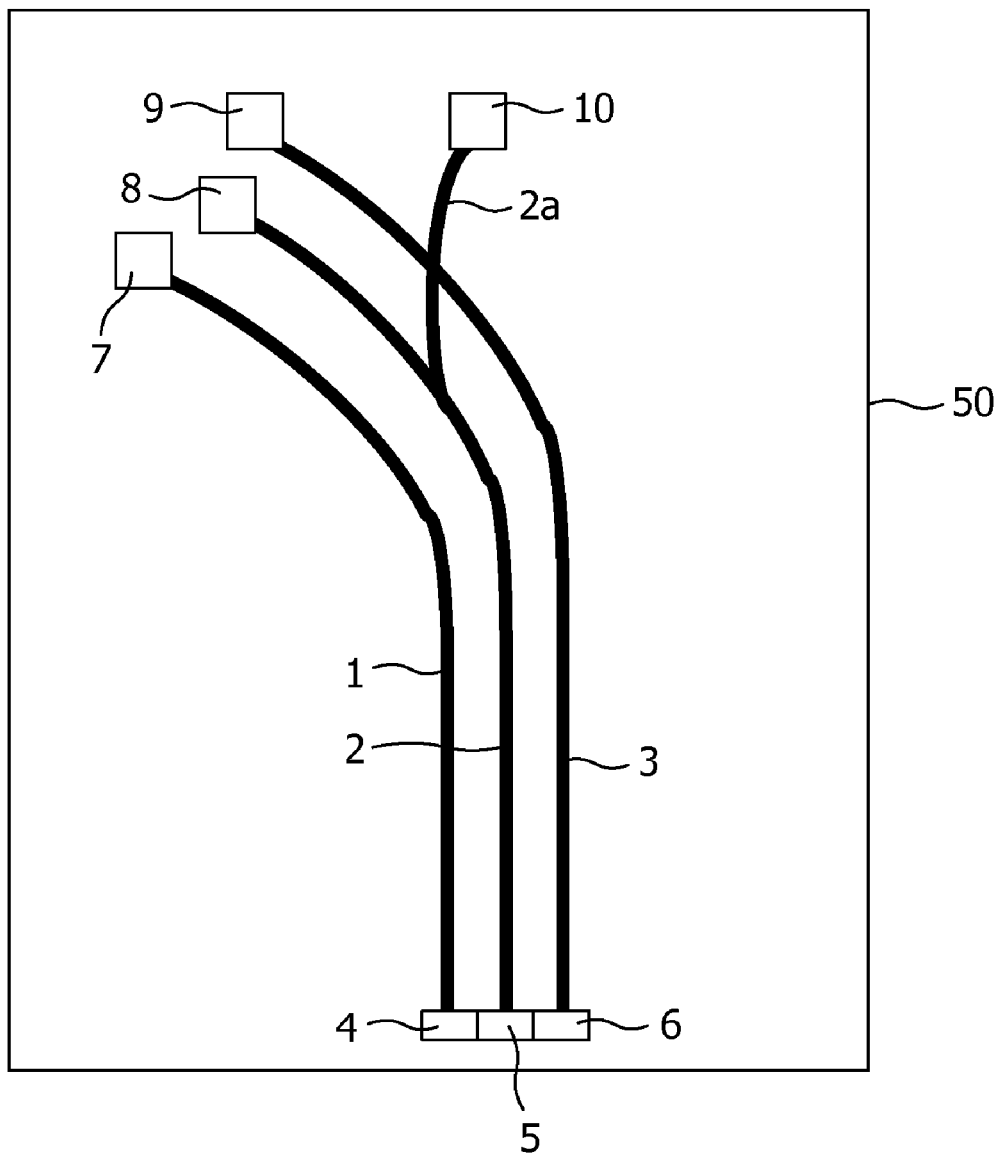
FIG. 4 is a schematic illustration showing a system according to an embodiment.

In another embodiment, according to FIG. 4, the system 50 LSS and DPS modalities are combined and integrated into one set-up. An advantage of this embodiment is that both measurements are done at exactly the same position, which will make correlations, or lack of correlation, between LSS and DPS spectra more pronounced. Another advantage is that the total number of fibers will be reduced as compared to separate LSS and DPS measurements. One aspect to take into account when creating a combined LSS and DPS modality is that polarization maintaining (PM) fibers, work for single mode only, i.e. one polarization orientation only. Therefore, PM fibers may only be used to deliver light, not to collect light. Otherwise, efficiency would be too low. Therefore, according to some embodiments a multimode fiber probe with a polarizer at the end of the probe is used. Such a multimode fiber probe is commercially available from e.g. Ocean Optics. In FIG. 4 the system set-up comprises fibers 1, 2 and 3 with polarizers 4, 5 and 6 at the end. Fiber 2 is denoted the excitation/detection fiber (same as DC fiber for DPS measurement) and the polarizer 5 at the end of this fiber transmits e.g. p polarized radiation. When a radiation excitation source 10 sends light into fiber 2 through a connection fiber 2a, the fiber 2 may be used for delivering (polarized) excitation radiation to the tissue sample. Fiber 1 is denoted 'perpendicular detection fiber', with its polarizer 4 perpendicular to the polarizer 5 of the excitation/detection fiber 2, which in this case may be an s-transmitting polarizer. Fiber 3 is denoted 'parallel detection fiber', with its polarizer 6 parallel to polarizer 5, which in the current example may be a p transmitting polarizer. Light that is collected by the fibers 1, 2 and 3 is sent to detectors 7, 8 and 9. These detectors may e.g. be spectrometers.

Figure 5:
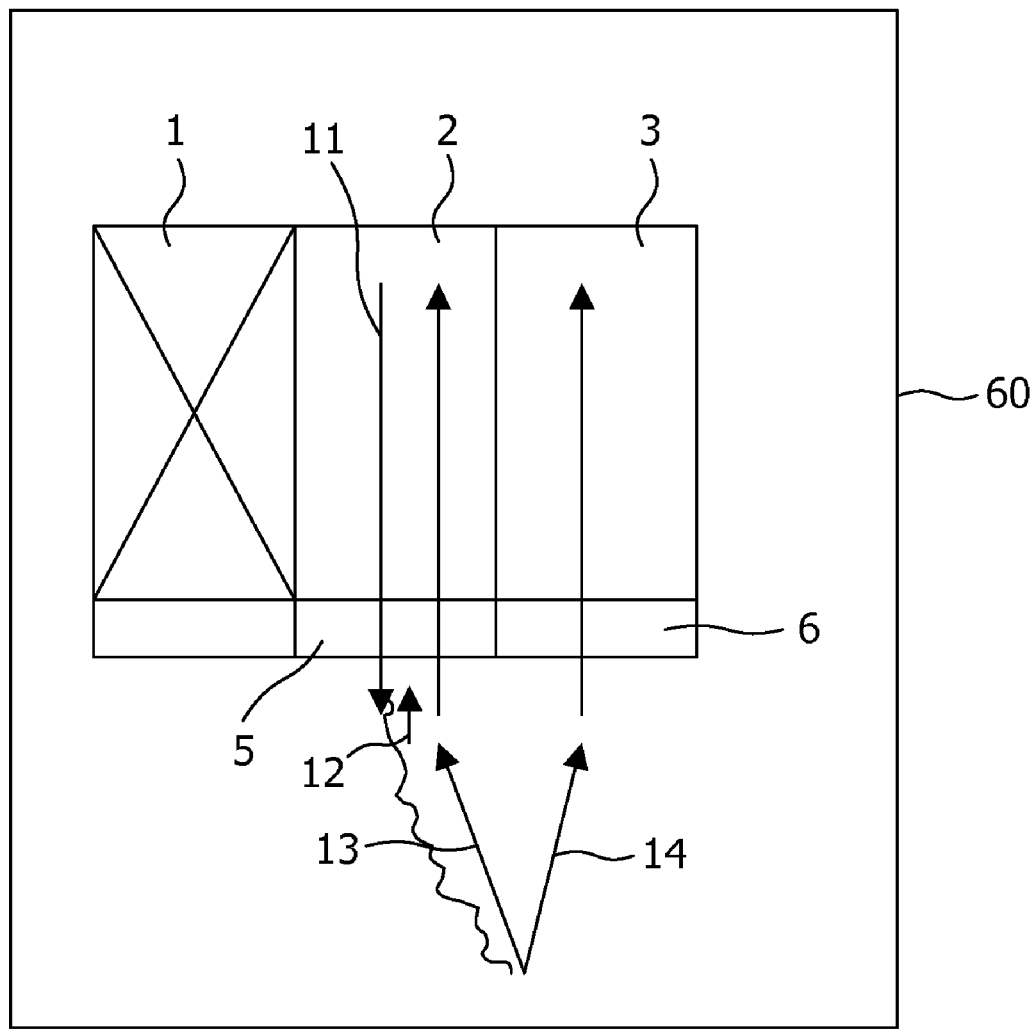
FIG. 5 is a schematic illustration showing a system according to an embodiment.

In an embodiment, according to FIG. 5, the system 60 may be operated in DPS mode. For operation in DPS mode only fibers 2 and 3 are used, which have both the same polarizer at its endpoints. FIG. 5 illustrates a simplified scheme of these two fibers. In the DPS operation mode excitation light 11 is directed onto the sample (not shown). The excitation light passes polarizer 5 before it arrives at the sample, and is thus polarized. From the sample, single scattered light 12 can immediately travel back into fiber 2 and since single scattered light keeps its polarization, polarizer 5 will not block the light 12. Further into the sample, under the influence of multiple scattering events, part of the light reaches fibers 2 and 3 (indicated with arrows 13 and 14). Upon reaching fibers 2 and 3, the multiple scattered light will be partially blocked, typically around 50%, because polarization of the excitation light is randomized due to multiple scattering. However, since both fibers measure these signals with the same efficiency, contributions from these two signals will be the same and by subtracting the signals from fiber 2 and 3 one gets the signal from the singly scattered photons.

A difference between the system and the conventional DSP modality is that also multiple scattered photons may preferentially reach fiber 2. This is the case for highly scattering media, and this is typically the case in biological samples such as for human skin wherein the scattering constant $\mu_s$ is with the range $10 < \mu_s < 100$ mm$^{-1}$. The difference is caused by polarizer 5 that blocks 50% of these multiple scattered photons. In practice this will optionally lead to a decrease in the constant differential pathlength, i.e. $1 \leq 0.80 \cdot d_{fibre}$. In other words, for a given probe depth the provided system may require a larger fiber diameter than conventional DPS.

Figure 6:
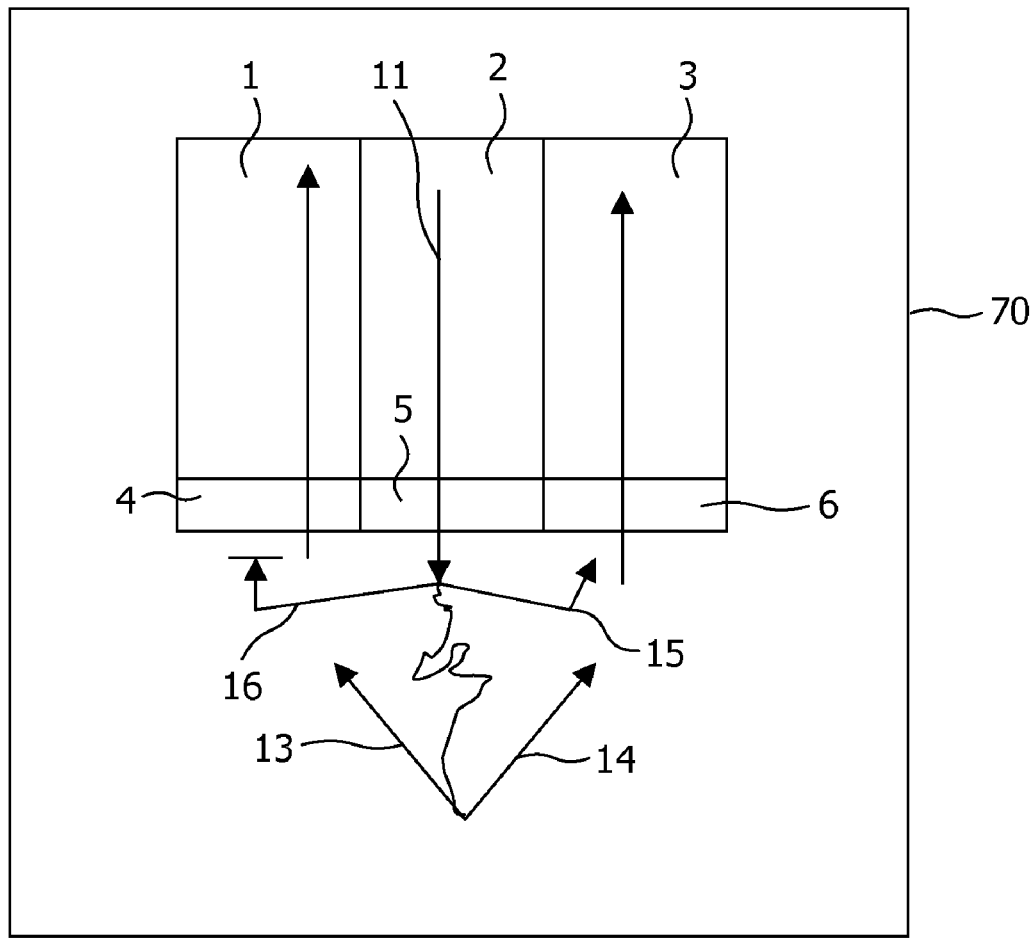
FIG. 6 is a schematic illustration showing a system according to an embodiment.

In another embodiment, according to FIG. 6, the system 70 is operated in LSS mode. In this mode of operation all three fibers are used. The centre fiber 2 is only used for excitation and the fibers 1 and 3 are used to detect scattered light from the sample. The excitation fiber 2 is exactly between the detection fibers 1 and 3, such that both fibers 1 and 3 will normally collect the same amount of radiation. However, because polarizers 4 and 6 are perpendicular to each other, both fibers will measure a different polarization. Thus, one fiber will return the signal for both singly and multiply scattered light, which in this case will be fiber 3. Fiber 3 detects the light indicated with arrow 15 and 14, while fiber 1 will only give a signal for multiply scattered light, indicated with arrow 13, with the singly scattered contribution 16 blocked by polarizer 4, due to the singly scattered light has kept its polarization. Subtracting the signals from fibers 4 and 6 will result in cancellation of the multiple scattered components, and only the singly scattered signal will remain.

In an embodiment the system 50 is operated for recording of LSS and DPS spectra in synchronization with pulsation. In this embodiment, recording of LSS and DPS spectra is synchronized with pulsation to eliminate fluctuation of blood oxygen concentration due to pulsation. According to this embodiment, sending probing light and recording spectra are triggered by a pulse detector (e.g. acoustic sensors or pressure sensors) with proper delay setting. To achieve a high signal to noise ratio, spectra may be sampled repeatedly at the same rate as pulsation of a patient.

In an embodiment the system comprises a console unit that may be used to control the units and measurements of the system. The console may e.g. be a touch screen display where a user interactively may perform the staging of cancer. In other embodiments the console is configured to perform the cancer staging automatically. The process status, calculated parameter values, etc may be displayed on the console.

In an embodiment the optical system is integrated into a catheter. The catheter may comprise at least one of the fibers 1, 2, or 3, and may be used in order to be able to deliver the fibers to the diagnosis site in vivo, e.g. in the bladder or stomach of a patient. In another embodiment at least one of the fibers 1, 2, or 3, may be provided in an endoscope for delivery to the diagnosis site in vivo.

Figure 7:
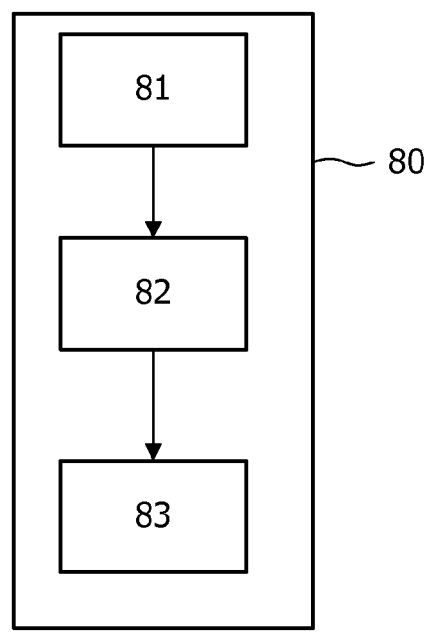
FIG. 7 is a block diagram showing a computer-readable medium according to an embodiment.

In an embodiment, according to FIG. 7 a computer-readable medium 80 is provided having embodied thereon a computer program for processing by a processor. The computer program comprises a first code segment 81 for performing a Polarized Light Scattering Spectroscopy measurement having a first probe depth, resulting in a first spectrum. Moreover the computer-readable medium comprises a second code segment for performing a Differential Path Length Spectroscopy measurement having a second probe depth, resulting in a second spectrum, wherein the second probe depth is larger than the first probe depth. Furthermore, the computer-readable medium comprises a third code segment for calculating a first correlation parameter value based on a correlation calculation of the first spectrum with a first reference spectrum, and a second correlation parameter value based on a correlation calculation of the second spectrum with a second reference spectrum. The first correlation value in relation to the second correlation value is indicative of the cancer stage of the investigated tissue.

In an embodiment the computer-readable medium comprises code segments arranged, when run by an apparatus having computer-processing properties, for performing all of the method steps defined in some embodiments.

Figure 8:
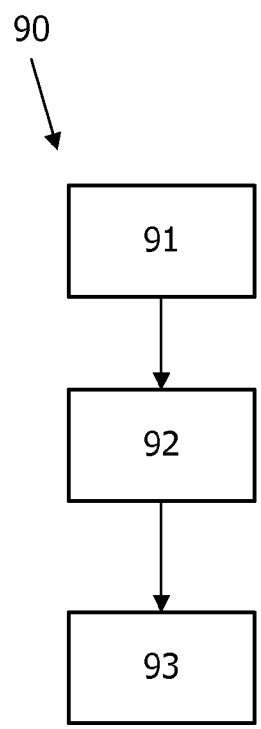
FIG. 8 is a block diagram showing a method according to an embodiment.

In an embodiment according to FIG. 8 a method for detection of early stages of epithelial cancer in a tissue of a patient is provided. The method comprises performing a Polarized Light Scattering Spectroscopy measurement 91 having a first probe depth, resulting in a first spectrum. Moreover the method comprises performing a Differential Path Length Spectroscopy measurement 92 having a second probe depth, resulting in a second spectrum, wherein the second probe depth is larger than the first probe depth. Furthermore, the method comprises calculation 93 of a first correlation parameter value based on a correlation calculation of the first spectrum with a first reference spectrum, and a second correlation parameter value based on a correlation calculation of the second spectrum with a second reference parameter. The first correlation value in relation to the second correlation value is indicative of the cancer stage of the tissue.

As mentioned above the LSS or DPS reference spectrum may be collected from e.g. a database having different parameter values for different types of tissue being in different stages etc.

In an embodiment the light source is a broadband Light Emission Diode (LED), laser, halogen lamp, xenon lamp, gas discharge lamp.

The present invention may according to some embodiments be applied for detection of epithelial cancers, tissue aberrations that may lead to cancer, or tissue aberrations that may indicate, or lead to other disorders. The fiber diameter, and indirectly the DPS probe depth, should be chosen according to the epidermis thickness of the particular tissue under study.

In an embodiment the processing unit is configured to perform a correlation C between the first spectral function f, corresponding to a first LSS (or DPS) spectrum, and the second spectral function g, corresponding to a second DPS (or LSS) spectrum, may be calculated with normalization according to the following:

$$C(L1, L2) = \int_{L1}^{L2} \left| \frac{g(L)}{g_0} - \frac{f(L)}{f_0} \right| dL, \qquad \text{(eqn. 1)}$$

$$g_0 = \int_{L1}^{L2} g(L) dL$$

$$f_0 = \int_{L1}^{L2} f(L) dL$$

wherein (f) is the reference LSS or DPS spectrum (e.g. LSS or DPS reference spectral function), and (g) is the measured LSS or DPS spectrum describing a measured LSS or DPS spectral function as a function of the wavelength (L, in micrometer). An optical sub band is defined by the wavelengths L1 to L2. As mentioned above at least one correlation will be performed for the LSS measurement and at least one correlation will be performed for the DPS measurement, such that there will be two resulting correlation values being indicative of the cancer stage of the investigated tissue. The final correlation of the first and second correlation value may be performed visually or automatically in order to diagnose the stage of cancer in the investigated tissue.

As the correlation C(L1, L2) approaches towards zero the better the correlation will be. When the two functions g and f correlates poorly the value of C(L1, L2) may e.g. be close to the value of 2. The processing unit according to some embodiments may also utilize any commonly known method of calculating the correlation C that is readily available to the skilled person. Hence the present invention according to some embodiments is not limited to the above-mentioned correlation equation (eqn. 1).

The processing unit may be any unit normally used for performing the involved tasks, e.g. a hardware, such as a processor with a memory. The processor may be any of variety of processors, such as Intel or AMD processors, CPUs, microprocessors, Programmable Intelligent Computer (PIC) microcontrollers, Digital Signal Processors (DSP), etc. However, the scope of the invention is not limited to these specific processors. The memory may be any memory capable of storing information, such as Random Access Memories (RAM) such as, Double Density RAM (DDR, DDR2), Single Density RAM (SDRAM), Static RAM (SRAM), Dynamic RAM (DRAM), Video RAM (VRAM), etc. The memory may also be a FLASH memory such as a USB, Compact Flash, SmartMedia, MMC memory, MemoryStick, SD Card, MiniSD, MicroSD, xD Card, TransFlash, and MicroDrive memory etc. However, the scope of the invention is not limited to these specific memories.

In an embodiment the system is comprised in a medical workstation or medical system, such as a diagnostic or therapeutic medical system.

In an embodiment a use of the system, method, computer-readable medium, or catheter fiber is provided for diagnosis and staging of early cancer aberrations.

The invention may be implemented in any suitable form including hardware, software, firmware or any combination of these. However, preferably, the invention is implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A system for detection of early stages of epithelial cancer in a tissue of a patient, said system comprising:
a Polarized Light Scattering Spectroscopy unit for performing a Polarized Light Scattering Spectroscopy measurement having a first probe depth, resulting in a first spectrum,
a Differential Path Length Spectroscopy unit for performing a Differential Path Length Spectroscopy measurement having a second probe depth, resulting in a second spectrum, wherein
said second probe depth is larger than said first probe depth, and
a processing unit for calculation of a first correlation parameter value based on a correlation calculation of said first spectrum with a first reference spectrum, and a second correlation parameter value based on a correlation calculation of said second spectrum with a second reference spectrum, wherein
said first correlation value in relation to said second correlation value is indicative of a cancer stage of said tissue.

2. The system according to claim 1, wherein said Polarized Light Scattering Spectroscopy unit and said Differential Path Length Spectroscopy unit utilize a first fiber for emitting light radiation originating from a light source on said tissue.

3. The system according to claim 2, wherein at least one of said first fiber and a second fiber or a third fiber is configured with a polarizer, said Polarized Light Scattering Spectroscopy unit being configured to receive scattered light radiation via the second fiber and the third fiber having different polarity, respectively.

4. The system according to claim 2, wherein at least one of said first fiber, a second fiber, or a third fiber being in connection with a detector configured to register received scattered light radiation, said Polarized Light Scattering Spectroscopy unit being configured to receive the scattered light radiation via the second fiber and the third fiber.

5. The system according to claim 2, wherein said second probe depth is adjustable by a selection of a size of a fiber core diameter of the first fiber.

6. The system according to claim 1, wherein said Polarized Light Scattering Spectroscopy unit is configured to receive scattered light radiation via a second fiber and a third fiber having different polarity, respectively.

7. The system according to clam 6, comprising a catheter or endoscope having a cavity configured to comprise at least one of said first fiber, said second fiber, or said third fiber.

8. The catheter or endoscope according to claim 7, being comprised in a medical workstation or medical system, such as a diagnostic or therapeutic medical system.

9. The system according to claim 1, wherein said Differential Path Length Spectroscopy unit is configured to receive scattered light via, a first fiber and a second fiber, wherein said first fiber and said second fiber having the same polarity, respectively.

10. The system according to claim 1, wherein the second probe depth is larger than the epithelial layer of the tissue of the patient.

11. The system according to claim 10, wherein the second probe comprises a fiber having a fiber core diameter ($d_{fiber}$) and the second probe depth $z_{max}$ satisfies $z_{max}=0.40*d_{fiber}$.

12. The system according to claim 1, enabling discrimination between the hyperplastic stage, dysplastic stage, carcinoma in situ, and carcinoma for said tissue.

13. The system according to claim 1, wherein said processing unit utilizes a correlation integral or principal component analysis to correlate said first spectrum and said second spectrum.

14. The system according to claim 1, wherein said correlation calculation utilizes the following equation:

$$C(L1, L2) = \int_{L1}^{L2} \left| \frac{g(L)}{g_0} - \frac{f(L)}{f_0} \right| dL,$$

$$g_0 = \int_{L1}^{L2} g(L) dL$$

$$f_0 = \int_{L1}^{L2} f(L) dL.$$

15. The system according to claim 1, wherein said Polarized Light Scattering Spectroscopy measurement and said Differential Path Length Spectroscopy measurement is synchronized with pulsation.

16. The system according to claim 1, further comprising a console unit configured to control said Polarized Light Scattering Spectroscopy unit, Differential Path Length Spectroscopy unit, or said processing unit.

17. A non-transitory computer-readable medium embodying computer instructions for processing by a processor, said computer program comprising
   a first code segment for performing a Polarized Light Scattering Spectroscopy measurement having a first probe depth, resulting in a first spectrum,
   a second code segment for performing a Differential Path Length Spectroscopy measurement having a second probe depth, resulting in a second spectrum, wherein said second probe depth is larger than said first probe depth, and
   a third code segment for calculating a first correlation parameter value based on a correlation calculation of said first spectrum with a first reference spectrum, and a second correlation parameter value based on a correlation calculation of said second spectrum with a second reference spectrum, wherein said first correlation value in relation to said second correlation value is indicative of a cancer stage of said tissue.

18. A method for detection of early stages of epithelial cancer in a tissue of a patient, said method comprising
   performing a Polarized Light Scattering Spectroscopy measurement having a first probe depth, resulting in a first spectrum,
   performing a Differential Path Length Spectroscopy measurement having a second probe depth, resulting in a second spectrum, wherein said second probe depth is larger than said first probe depth, and
   calculating a first correlation parameter value based on a correlation calculation of said first spectrum with a first reference spectrum, and a second correlation parameter value based on a correlation calculation of said second spectrum with a second reference spectrum, wherein said first correlation value in relation to said second correlation value is indicative of a cancer stage of said tissue.

* * * * *